United States Patent
Frenken et al.

(12)

(10) Patent No.: US 6,517,829 B1
(45) Date of Patent: Feb. 11, 2003

(54) PRODUCTS COMPRISING INACTIVATED YEASTS OR MOULDS PROVIDED WITH ACTIVE ANTIBODIES

(75) Inventors: Leon Gerardus Joseph Frenken, Vlaardingen (NL); Michael Marie Harmsen, Lelystad (NL); Richard Hendricus Jacobus van der Linden, Utrecht (NL); Cornelis Theodorus Verrips, Vlaardingen (NL)

(73) Assignee: Unilever Patent Holdings BV, Vlaardingen (NL)

( * ) Notice: Subject to any disclaimer, the term of this patent is extended or adjusted under 35 U.S.C. 154(b) by 0 days.

(21) Appl. No.: 09/266,805

(22) Filed: Mar. 12, 1999

(30) Foreign Application Priority Data

Mar. 12, 1998 (EP) .............................. 98104479

(51) Int. Cl.⁷ .................... A01N 63/00; A61K 47/00; A61K 39/40; A61K 39/108; A23K 1/17
(52) U.S. Cl. ................ 424/93.21; 424/93.51; 424/439; 424/442; 424/150.1; 424/241.1; 424/803; 426/623; 426/630; 426/635; 426/442
(58) Field of Search ................ 424/442, 439, 424/157.1, 803, 150.1, 261.1, 93.21, 93.51, 93.5; 426/623, 442, 630, 635, 20, 805

(56) References Cited

U.S. PATENT DOCUMENTS

| | | | | |
|---|---|---|---|---|
| 4,600,706 A | * | 7/1986 | Carter | 514/31 |
| 4,877,615 A | * | 10/1989 | Vandenbergh et al. | 424/115 |
| 5,433,947 A | * | 7/1995 | Harman et al. | 424/94.61 |
| 5,627,072 A | * | 5/1997 | Leenhouts et al. | 435/320.1 |
| 5,989,584 A | * | 11/1999 | Cook et al. | 424/442 |
| 6,068,862 A | * | 5/2000 | Ishihara et al. | 426/2 |
| 6,120,732 A | * | 9/2000 | Toledo et al. | 422/39 |

FOREIGN PATENT DOCUMENTS

| | | | | |
|---|---|---|---|---|
| EP | 0 739 981 A1 | 10/1996 | | C12N/15/13 |
| EP | 0 899 326 | * | 3/1999 | |
| WO | WO 94/18330 | 8/1994 | | C12N/15/62 |
| WO | WO 94/25591 | 11/1994 | | C12N/15/13 |
| WO | WO 94/29457 | 12/1994 | | C12N/15/62 |

OTHER PUBLICATIONS

Penley et al. Dev. Ind. Microbiol. 24: 369–375, 1983.*
Gudmundsdottir. SIK Report 582: 1–73, 1991.*
Kociova et al. Hydinarstvo 25: 37–46, abstract, 1990.*
Ohkawa et al. Br. J. Urol. 66: 22–25, abstract, 1990.*
Ananthnarayan et al. Textbook of Microbiology, Orient Longman, Patna, pp. 26–38, 1978.*
Ananthanarayan et al. Textbook of Microbiology, Orient Longman, New Delhi, 1978, pp. 547–550.*
Henning et al. Int. J. Food Microbiol. 3: 121–134, 1986.*
Talwar et al. Mycopathologia 94: 39–44, abstract, 1986.*
Spinelli et al. Nature Struct. Biol. 3: 752–757, Sep., 1996.*
Schreuder et al. TIBTECH 14: 115–120, 1996.*
Davies et al, Protein Engineering, vol. 9, No. 6, pp. 531–537 (1996).

* cited by examiner

*Primary Examiner*—S. Devi
(74) *Attorney, Agent, or Firm*—Morgan, Lewis & Bockius LLP (57) ABSTRACT

New products are provided comprising inactivated lower eukaryotic cells, preferably yeasts or molds, having at the outer surface functionally active antibodies or functionally active fragments thereof. Preferred antibody fragments are the variable domains of Camelidae heavy chain antibodies, which are surprisingly stable against physical and chemical decontamination regimes and do not loose their activity when they are immobilized on the glucan layer of the cell wall which is present in a variety of lower eukaryotes. The new products are preferably in the field of food products, personal care products, and animal feed products.

22 Claims, 4 Drawing Sheets

Fig.4B.
VHH hCG

Fig.4D.
VHH RR-6

Fig.4A.
Mab hCG

Fig.4C.
Mabs RR-6

PRODUCTS COMPRISING INACTIVATED YEASTS OR MOULDS PROVIDED WITH ACTIVE ANTIBODIES

FIELD OF THE INVENTION

The present invention is in the field of applied biotechnology and relates in particular to an economic way of introducing antibodies into a variety of products, especially food and animal feed. The invention further relates to such products.

BACKGROUND OF THE INVENTION

To fulfil many unmet demands of the society, there is a clear need to provide new products from which consumers may benefit, in particular in the field of food products including animal feed. One of the problems with the presently used consumer products is that if they contain functional compounds, these compounds are not very specific.

For instance, for killing microorganisms in food products the functional compound may be salt or acid. When the concentration of either of these compounds is sufficiently high, they are able to kill microorganisms. However, often the level of salt makes the taste of the product less attractive to the consumer. Moreover, high levels of salt are not recommended by health authorities. The same holds for products that contain considerable amounts of acids or preservatives.

Non-food consumer products such as laundry products may contain compounds that are able to bleach stains, but as they do not specifically recognise stains, considerable amounts of these bleach generating compounds (e.g. percarbonate/TAED) are necessary.

Another example is that some personal hair care products contain compounds that kill the microorganisms involved in dandruff. Also these compounds are not specific and in addition to the causative microorganisms of dandruff they also kill other microorganisms on the skin which are beneficial to the consumer.

Still another example of an unmet demand of the society is the overproduction of manure due to cattle farming. Part of this problem is that the conversion of animal feed into nutrients is not optimal due to the presence of negative compounds like fytic acid.

The above given examples of unmet consumer needs and society seeds can be extended, but it will already be clear that consumer-products and animal feed with compounds which specifically meet the demand of the consumer or society will be of great importance.

The main characteristic of processes in living cells or living species is that they are highly specific. Enzymes just recognise specific substrates and the specificity of antibodies is unsurpassed. Therefore in recent years the industries involved in the manufacturing of (chemical and biotechnological) consumer products or animal feed are increasingly applying biological molecules in order to make their products more specific.

A successful example of this development is the introduction of proteases, lipases, cellulases and amylases in laundry products. These enzymes have a certain specificity and because the production of these enzymes has been improved considerably by recombinant DNA techniques, these microbial enzymes can be produced by microorganisms at costs affordable for consumer products. The introduction of enzymes in detergents has indeed met demands of our society. Over the last decades the energy usage for cleaning of laundry has been reduced with about 50% and the amount of chemicals with about 40%.

In the area of animal feed enzymes can play an important role to reduce the environmental pollution, as has been nicely demonstrated by the application of the enzyme fytase in animal feed. Again this development was possible due to the enormous improvement of the production of fytase by rDNA techniques.

However, often a higher specificity than just recognising a protein or fat is highly desirable to fulfil the unmet demands and therefore the consumer goods and animal feed industry is looking for ways to get specificities in the same order as antibodies have.

In nature microorganisms do not produce antibodies. Although it is well known that by using rDNA technology microorgansims can produce almost any protein, irrespective of its origin, the yield of homologous proteins is much higher than for heterologous proteins. Moreover, expensive purification processes are needed to recover the heterologous protein from its producing cell, since it is not allowed to bring living rDNA organisms into the environment. These two factors, the low production yield and the fact that rDNA organisms have to be separated from the products that they produce have slowed down the introduction of heterologous proteins in consumer products other than in laundry products and some food products. In animal feed only the addition of fytase is a real success up to now.

The present invention relates in particular to introducing certain categories of antibodies into a variety of products, especially food and animal feed.

In WO 94/18330 a method is disclosed for immobilizing a binding protein to the exterior of the cell wall of a microbial host cell, in particular a lower eukaryote, by producing a fusion protein which binds to the anchoring part of a cell wall anchoring protein, thereby ensuring that the binding protein is localized in or at the exterior of the cell wall of the host cell. The binding proteins may ligate or bind to the specific compound to be isolated since they have specific recognition of such compounds or compounds related therewith. Examples of binding proteins mentioned in this reference include antibodies, antibody fragments, combinations of antibody fragments, receptor proteins, etc.

Similarly, WO 94/01567 discloses a method for immobilizing an enzyme to the exterior of the cell wall of a microbial host cell, in particular a lower eukaryote.

Hamers-Casterman et al., *Nature* (1993) 363:446–448 disclose isolated immunoglobulins from the serum of camelids comprising two heavy polypeptide chains sufficient for the formation of a complete antigen binding site, which immunoglobulins further being devoid of light polypeptide chains.

WO 94/25591 discloses the production of antibodies or functionalised fragments thereof derived from heavy chain immunoglobulins of Camelidae, using transformed lower eukaryote host organisms. The term "functionalized fragment" was used for indicating an antibody or fragment thereof to which one or more functional groups, including enzymes and other binding polypeptides, are attached resulting in fusion products of such antibody fragment with another biofunctional molecule. The same definition will be used herein for the present invention.

Spinelli et al., *Nature structural biology* (1996) 3:752–757 disclose the crystal structure of a llama heavy chain variable domain.

In many processes involving recombinant DNA techniques and culturing or fermenting transformed microorganisms, it is necessary at some stage, for example at the conclusion of the fermentation, to kill the active cells in order to prevent any viable recombinant organisms from being released into the environment.

A conventional way of killing cells is using heat. U.S. Pat. No. 4,601,986 is an example of the use of heat to kill the cells and stop the growth of microorganism cultures. Other conventional ways of killing cells are by lysing the cells, for example by changing the osmotic pressures or by adding enzymes which break down the cell walls or membranes. These techniques are exemplified in U.S. Pat. Nos. 4,299,858, 3,816,260, 3,890,198, and 3,917,510, the disclosures of which are incorporated herein by reference.

In many systems host microorganisms, for example lower eukaryote cells, are difficult to kill. Conventional methods, such as heat, are too severe and may destroy or alter the desired product before the cells are killed. This applies also for the immobilized systems of binding proteins on lower eukaryotes disclosed in WO 94/18330, when the binding protein is an antibody or a functional fragment thereof.

Therefore, there is still a need for stable functional systems involving transformed microorganisms, where the microorganisms are inactivated or killed while the functional activity of the system is substantially maintained. The present invention provides such a stable functional system.

SUMMARY OF THE INVENTION

In accordance with the present invention there is provided a product, preferably selected from the group consisting of food products, personal care products, and animal feed products, comprising inactivated recombinant lower eukaryotic cells having at least at their outer surface functionally active antibodies, or functionally active fragments of antibodies.

In a preferred embodiment of the invention, the antibodies or, more preferably, antibody fragments are heavy chain antibodies from Camelidae or the variable domain of these antibodies The lower eukaryotic cells are substantially inactivated by either one or more physical techniques or chemical treatment, or a combination of physical and chemical treatment. The lower eukaryote cells are preferably inactivated with a factor>$10^6$ by physical treatment. Chemical treatment comprises the action of an effective amount of at least one of an antimicrobial agent, for example sorbic acid, benzoic acid, nisin, MB21, or another bacteriocin, and a cell wall degrading enzyme, for example β-(1,3)-glucanase, β-(1,6)-glucanase, chitinase, or a redox enzyme, or a combination of one or more antimicrobial agents and one or more cell wall degrading enzymes.

In another preferred embodiment of the invention, the antibody fragments recognise harmful microorganisms or toxins with a binding constant of >$10^6$, preferably >$10^7$, most preferably >$10^8$.

In another preferred embodiment according to the invention there are provided animal feed products containing killed yeast cells having on their surface one or more functional anti-animal pathogenic microorganisms, for example E. coli, Salmonella, Shigella, and animal viruses. In a preferred embodiment there are provided animal feed products containing inactivated yeast cells having functional anti-E. coli K88 llama antibodies on their surface that protect animals against this pathogenic bacterium.

These and other aspects of the invention will be described in further detail in the description which follows.

DETAILED DESCRIPTION OF THE INVENTION

Complete antibodies, consisting of two heavy and two light chains are rather stable as they have to circulate in the blood and lymph systems to protect the host against invaders. This stability is caused by several S—S bridges between the heavy chains and the strong interaction between the heavy and the light chain. However, production of complete antibodies in microorganisms is very difficult and economically not feasible for introduction into consumer products or animal feed.

Recently, it has been shown that antibody fragments of "traditional" antibodies can be produced by certain microorganisms (supra), but in general the yield of these fragments is rather low. The stability of fragments of traditional antibodies (defined as a single chain of a heavy and a light chain, with a linker between them) is rather low and the physics of protein stability is still not sufficiently developed to predict protein stability from its amino acid sequence.

It has also been shown that the variable domain of antibodies of Camelidae which consist of only one heavy chain can be suitably produced by micoorganisms. In particular, they can be produced very well on the cell wall of lower eukaryotes. Cell wall proteins which typically have a glycophosphatidylinositol (GPI) anchor, are secreted by lower eukaryotes via a different secretion pathway as compared to normal secreted proteins. Whereas stability of pure proteins cannot be predicted on the basis of their amino acid sequence yet, the effect of linking proteins to the glucan layer on their stability is even more unknown and unpredictable.

The present invention is based on the surprising finding, after extensive research and experimentation, that the variable domains of Camelidae heavy chain antibodies are more stable against higher temperatures as compared with the variable domains of traditional antibodies. It is even more surprising that certain variable domains of Camelidae antibodies from llamas appear to be very stable under pasteurisation conditions. Furthermore, the specific properties of these antibodies or antibody fragments are substantially maintained when they are immobilised on the glucan layer of cell walls which are present in a large variety of lower eukaryotes. Immobilisation of these antibodies, or their variable fragments, on the cell wall of lower eukaryotes does not just ensure a good production yield, but also offers the possibility of separating these lower eukaryotes from the fermentation liquid either by centrifugation or filtration. Both centrifugation and filtration processes are relatively cheap and are applied in the manufacture of compounds for consumer products and animal feed.

The invention is further based on the finding that physical techniques and chemical treatment, or a combination of physical techniques and chemical treatment or a combination of special types of mild techniques is able to kill these lower eukaryotes, typically with a factor >$10^6$, whereas the antibody fragments retain their functionality to a large extent, typically >60%, and preferably from about 70% to 100%. Reduction with a factor of at least $10^6$ is desired, because this killing efficiency is often acceptable for the health authorities as killing efficiency for pathogenic bacteria in food products. A preferred reduction is with a factor of $10^{-7}$ to $10^{-9}$.

Therefore, in one aspect of the present invention there is provided a product, preferably selected from the group consisting of food products and animal feed products, comprising inactivated lower eukaryotic cells having at their outer surface functionally active antibodies, or functionally active fragments of antibodies.

In another aspect of the present invention, it has been found that immobilising these antibody fragments to the glucan layer of lower eukaryotes do not decrease the temperature stability to such an extent that immobilised llama antibody fragments will loose their functionality during pasteurisation.

Although heat is by far the most widely applied physical decontamination technique in the consumer product industry, the stability of these immobilised antibodies was also tested against ultra high pressure, pulse electric field and radiation. For all these physical decontamination techniques conditions were found in which the lower eukaryote was killed with an efficiency of >$10^6$, whereas the antibody fragment retained over 70% of its functionality.

In still another aspect of the invention it was found that combinations of mild physical treatments and antimicrobial compounds, such as acids or antimicrobial peptides were even more effective to kill the lower eukaryotes, while maintaining the functionality of the Camelidae antibody fragment. Using these combinations, killing effects of >$10^7$ could be achieved, while the functionality of the antibody remained substantially unaffected.

Mouse monoclonal antibodies (MAbs) or fragments thereof have many potential applications in addition to for example cancer therapy and diagnostic kits. However, for most applications large quantities are needed whereas costs have to be reduced. For MAbs or fragments thereof these conditions often cannot be met. The Camelidae heavy-chain antibodies offer a solution to this problem. Probably because of their simple one chain structure and their solubility (Spinelli et al., 1996), the variable part of llama heavy chain antibodies ($V_{HH}$; also referred to as "HCV" or "H-CV") can be secreted relatively pure and in high amounts by the yeast S. cerevisiae. For this reason, llama antibody $V_{HH}$s are suitable for large scale applications.

As will be shown in the experimental part, llama $V_{HH}$s are far more heat stable compared to mouse MAbs. Most llama $V_{HH}$s were still able to bind after two hours at temperatures as high as 90° C. The thermal denaturation at lower temperatures of mouse MAbs can be explained because of heavy and light chain separation. After cooling down, these fragments will not associate, or only randomly, resulting substantially in non-functional antibodies.

In general, llama $V_{HH}$s and mouse MAbs are comparable in antigen binding in the presence of ATC. HCG specific antibodies could bind at higher ATC concentrations than RR-6 specific antibodies. This is probably due to the nature of the antigen and or antibody-antigen interaction. Regarding the specificity, llama $V_{HH}$s have about the same potential as mouse MAbs in recognition of antigen. Within the small subset of anti-hCG, llama $V_{HH}$s, some were found specific to separate alpha-subunit, beta-subunit and intact hCG. The anti-RR6 llama $V_{HH}$s did not crossreact with other azodyes, resembling RR-6 in structure. The small subset tested seems to be very specific to RR-6.

Most of the llama $V_{HH}$s have apparent affinities ($K_D$) range of $10^{-7}$–$10^{-9}$ M, which is of high affinity. Some mouse MAbs used were found to have higher affinity ($10^9$–$10^{11}$ $M^{-1}$) which can be contributed to avidity because mouse MAbs are bivalent.

In summary, when comparing the biochemical properties of llama $V_{HH}$s and mouse MAbs for stability, specificity and affinity, it appears that llama $V_{HH}$s have physical chemical properties which make them excellent candidates for use both in existing and novel applications. These applications are in a variety of fields and which are immediately evident to the man skilled in the art. As most food products have to be pasteurized, the addition of $V_{HH}$s create really new options. For example, $V_{HH}$s that bind and neutralize redox enzymes thereby preventing colour changes of food products, or $V_{HH}$s that recognize proteins or polysaccharide of food products thereby providing or improving the structure to the product, or $V_{HH}$s that bind off flavours (scavenging) or bind flavours (controlled release). However, also many personal care products are decontaminated by physical techniques like heat or pressure and in these personal care products $V_{HH}$s can be introduced as well and provide important benefits like recognition of acne causing microorganisms, scavenging of under-arm odours, etc. Preferred products in which $V_{HH}$s can be applied therefore include, for example, consumer products, such as food products and cosmetics (e.g. skin creams), and animal feed.

The preparation of the immobilized functionally active antibodies or functionally active fragments of antibodies on the outer surface of lower eukaryote cells (which term include yeasts, moulds and fungi) according to the present invention is similar to the preparation of immobilized binding proteins as described in WO 94/18330, the disclosure of which is incorporated herein by reference. The preparation of the specific Camelidae heavy-chain antibody fragments has also been described in the literature (supra, the disclosures of which are also incorporated herein by reference), so that the man skilled in the art can easily prepare these immobilized antibodies without applying inventive skill.

In a typical example of the present invention the Camelidae antibodies or functional antibody fragments are immobilized on α-agglutinin as the cell wall protein. It is to be understood, however, that also other cell wall ingredients are suitable to anchor the antibodies or antibody fragments, thereby maintaining substantially their primary function. Suitable cell wall ingredients include, for example, CWP1, CWP2, TIP1, SED1, TIR2, YCR89w, FLO1, AGa1, and AGA1; see Van der Vaart, J. M. and C. T. Verrips (1998), Cell wall proteins of S. cerevisiae, Biotechnology and Genetic Engineering Reviews 15:387–411.

Although the present invention has been described by typically applying lower eukaryotes as the carriers of the functionally active antibodies or functionally fragments of antibodies, disclosed herein, it will be evident to those skilled in the art, that also other inactivated organisms, such as bacteria (e.g. lactic bacteria), algae, tissue cultures and plants can be similarly used.

The invention is further illustrated by the following experimental work which however is not intended to limit the invention in any respect.

Materials and Methods

To investigate if llama antibodies can be used in a range of applications, a number of physical chemical and functional characteristics was investigated, thereby concentrating on three characteristics: stability, specificity and affinity. Llama $V_{HH}$s and "classical" bivalent mouse monoclonal IgG antibodies ("mouse MAbs"), specific for either the human pregnancy hormone or the azodye Reactive Red-6 ("RR-6"), were compared with respect to heat stability and antigen binding in chaotropic environment (ammonium thiocyanate, ATC elution). Furthermore, llama $V_{HH}$s were tested for their antigen specificity and affinity. Both llama and mouse antibodies consist of two subsets: one specific for the protein antigen human Chorionic Gonadotropin (hCG) and one specific for the hapten azodye RR-6.

The results show that llama $V_{HH}$s display similar functional characteristics with respect to specificity, affinity, and binding, in the presence of ammonium thiocyanate and ethanol, compared to "classical" mouse MAbs. However, especially regarding functional binding at high temperature (about 90° C.) llama $V_{HH}$s are extraordinarily stable, compared to mouse MAbs.

Purification of Llama $V_{HH}$s and Mouse MAbs

Llama $V_{HH}$s HI-6, H-13, H-14, HI-15, HI-113 (anti-hCG) and R2, R4, R7, R8, R9, R10 (anti RR-6), described in EMBL data library accession numbers: AJ236095 (HI-6), AJ236096 (H-13), AJ236094 (H-14), AJ236097 (HI-15), AJ236098 (HI-113), AJ236100 (R2), AJ236102 (R4), AJ236105 (R7), AJ236106 (R8), AJ236107 (R9), and AJ236108 (R10), were secreted by S. cerevisiae as a fusion protein comprising a $V_{HH}$ with a C-terminal myc-tag and a $(His)_6$-tag. For stability studies, yeast culture supernatants containing llama $V_{HH}$s were ultrafiltrated using membranes with cut off limits of 50 kD and 5 kD, respectively, (Filtron, USA) and dialysed against phosphate buffered saline (PBS, 145 mM NaCl, 7.5 mM $Na_2HPO_4$, 2.5 mM $NaH_2PO_4$, 0.01% sodium azide).

The final $V_{HH}$ preparation had a purity between 80–90% as judged by Coomassie Brilliant Blue (R-250, Sigma, Zwijndrecht, the Netherlands) staining of sodium dodecyl sulphate polyacrylamide gels (SDS-PAGE).

Mouse MAbs were obtained from hybridoma culture supernatant and purified using protein A and subsequent dialysis against PBS. The hCG specific mouse MAbs used was mAB 3299 (anti-Thyroid Stimulating Hormone). The RR-6 specific mouse MAbs used was URL 08-04.

Sub-saturation Point

Figure 1:
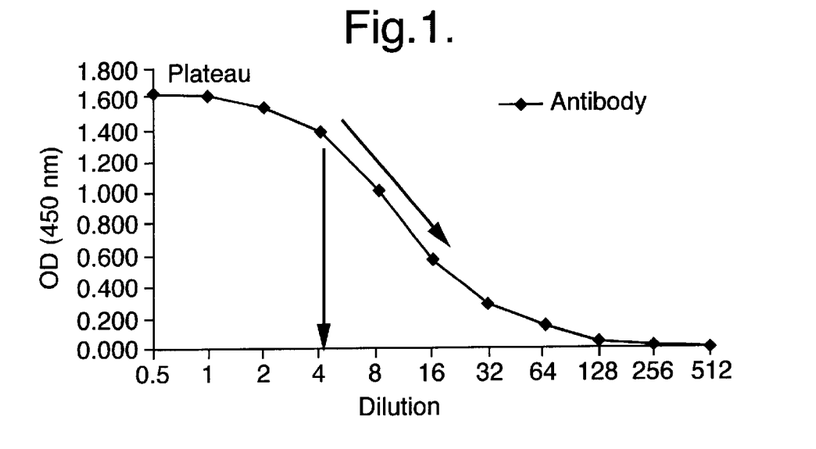
FIG. 1 shows a typical dilution curve for the antibodies used, from which the sub-saturation point was determined.
Figure 2A:
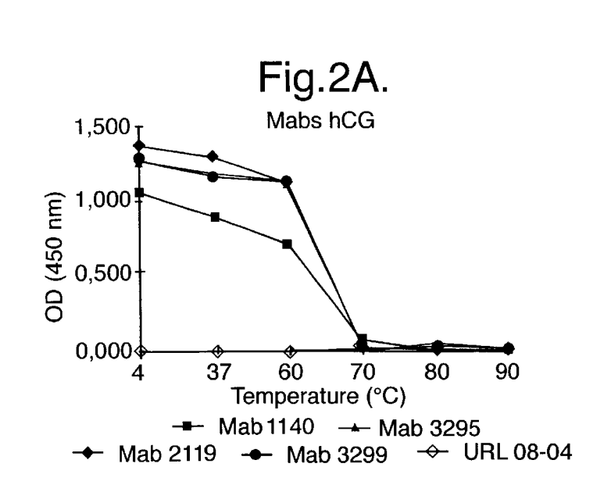
FIGS. 2A–2D show the antigen binding after temperature treatment of hCG specific mouse MAbs (A) and llama $V_{HH}$s (B) or RR-6 specific mouse MAbs (C) and llama $V_{HH}$s (D). Antibodies were incubated for 2 hrs at different temperatures, cooled down to room temperature and subsequently ELISA was performed.
Figure 2B:
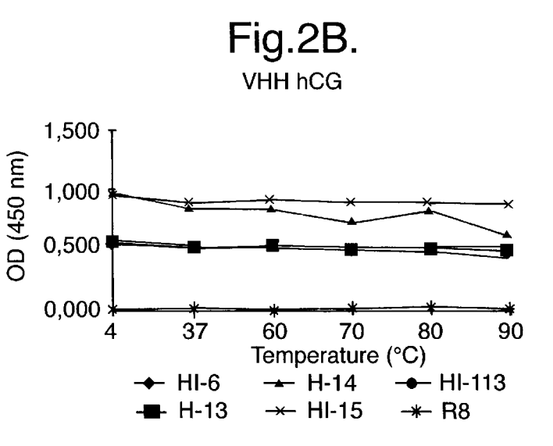
Figure 2C:
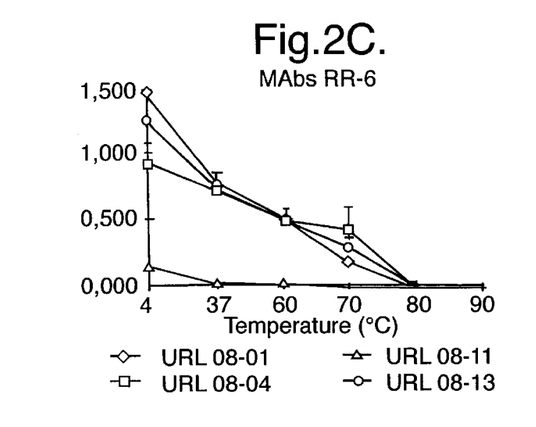
Figure 2D:
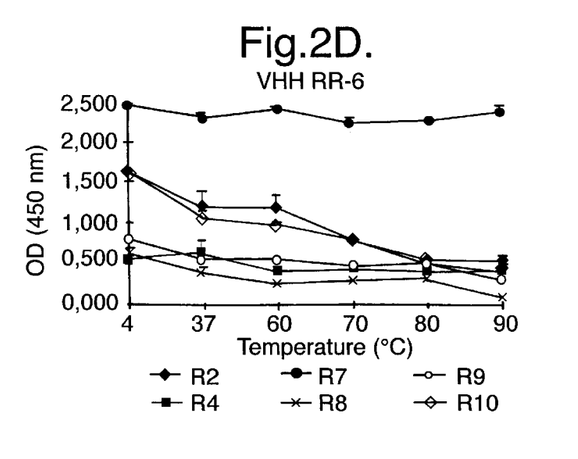

Using ELISA, dilution curves were made for all antibodies. From these dilution curves subsaturation point was determined (FIG. 1). The sub-saturation point was defined as the highest concentration on the linear part of the curve. Using this sub-saturation point any effect on antigen binding can be observed as a decrease in signal.

Temperature

Llama $V_{HH}$s and mouse MAbs were incubated at various temperatures (4° C., 60° C., 70° C., 80° C. and 90° C.) for two hours. Subsequently, antibodies were put 30 minutes at 25° C. and stored at 4° C. Samples were diluted to sub saturation point and ELISA was performed (FIG. 2). It can be concluded that the $V_{HH}$ fragments are more stable than the MAbs fragments.

Binding in the Presence of ATC

Double ATC (0–8M) concentrations were mixed 1:1 with double sub saturation concentrations of antibodies and were incubated for 10 min at room temperature. Standard ELISA was performed using antibody-ATC mixtures. See FIG. 3. In general, llama $V_{HH}$s and mouse MAbs are comparable in antigen binding in the presence of ATC. HCG specific antibodies could bind at higher ATC concentrations than RR-6 specific antibodies. This is probably due to the nature of the antigen and/or antibody-antigen interaction.

Figure 3A:
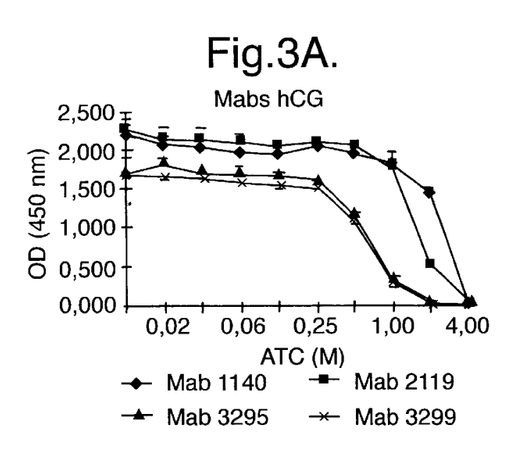
FIGS. 3A–3D show the antigen binding in presence of ammonium thiocyanate at sub saturation point of hCG specific mouse MAbs (A) and llama $V_{HH}$s (B) or RR-6 specific mouse MAbs (C) and llama $V_{HH}$s (D).
Figure 3B:
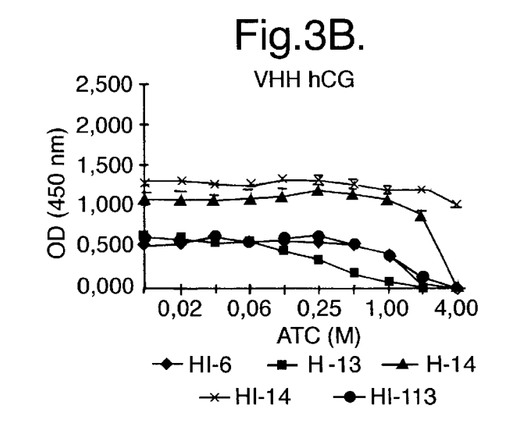
Figure 3C:
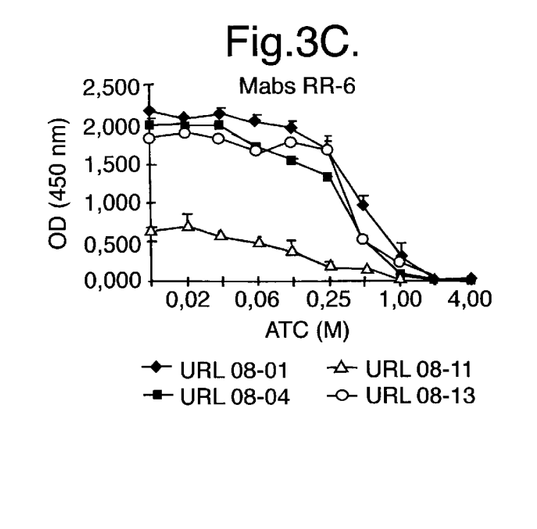
Figure 3D:
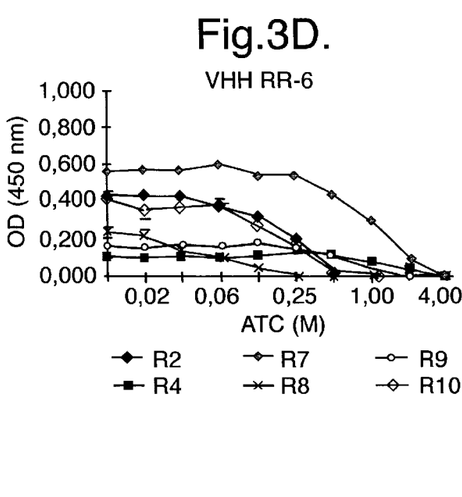
Figure 4A:
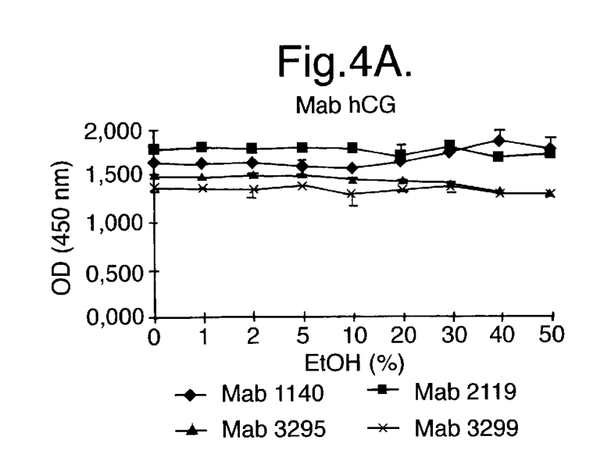
FIGS. 4A–4D show the antigen binding in the presence of ethanol at sub-saturation point of hCG specific mouse MAbs (A) and llama $V_{HH}$s (B) or RR-6 specific mouse MAbs (C) and llama $V_{HH}$s (D)
Figure 4B:
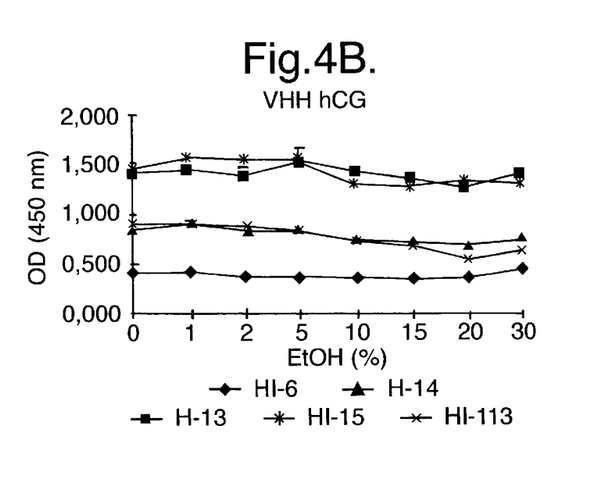
Figure 4C:
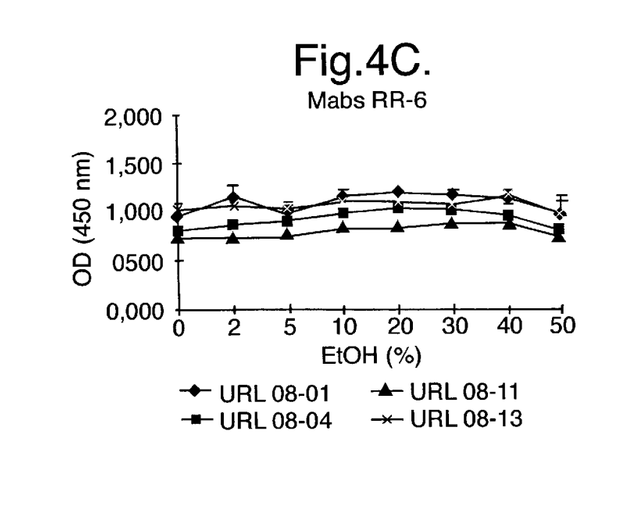
Figure 4D:
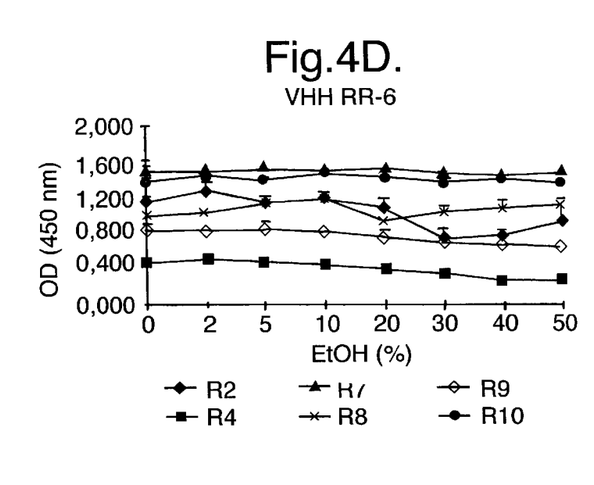

From FIGS. 3B and 3D it can be concluded that the llama $V_{HH}$ fragments HI-15 and R7 are able to bind at higher concentrations ammonium thiocyanate than any of the RR-6 or hCG specific mouse MAbs tested. The binding of HI-15 was reduced only 20% in 4M ammonium thiocyanate, whereas none of the other antibodies tested were able to bind at this concentration. Llama $V_{HH}$ fragment R7 was completely inhibited in RR-6 binding at 4M ammonium thiocyanate, whereas the best anti RR-6 Mabs (URL 08-01 and URL 08-13) were already completely inhibited at 2M ammonium thiocyanate (FIG. 3C).

Binding in the Presence of Ethanol

Using a comparable setup as for thiocyanate, antibody binding in increasing ethanol concentrations was tested. Both Llama $V_{HH}$s and mouse MAbs bound similarly to their antigen in the presence of ethanol at concentrations as high as 50% (FIG. 4). Neither llama $V_{HH}$s nor mouse MAbs were inhibited in binding at 50% ethanol. No difference was found between hCG and RR-6 specific antibodies, both llama and mouse. Only RR-6 specific llama $V_{HH}$ fragments R2 and R4 display a small decrease in binding above 30% ethanol.

Specificity of Llama $V_{HH}$s

ELISA was performed on separate alpha-, beta-subunit, or native hCG. The results are shown in Table 1.

TABLE 1

| Specificity llama $V_{HH}$S anti-hCG | | | |
|---|---|---|---|
| Llama $V_{HH}$ | Alpha | Beta | Intact |
| HI-6 | − | + | + |
| H-13 | + | − | + |
| H-14 | + | − | + |
| HI-15 | + | − | + |
| HI-113 | − | − | + |

Within this small subset, llama $V_{HH}$s were found specific to separate alpha, beta, or native hCG. This indicates that llama $V_{HH}$s have the same potential as mouse MAbs in recognition of antigen.

Affinity

Apparent affinities of a selection of llama $V_{HH}$s were determined by kinetic measurements using the IAsys Biosensor (Affinity Sensors, Cambridge, UK). The results are given in Table 2 below.

TABLLE 2

| Affinity values llama $V_{HH}$S and mouse MAbs | | | |
|---|---|---|---|
| Llama $V_{HH}$ | Kd (nM) | Mouse Mab | Kd (nM) |
| H-14 | 300–400 | URL 08-04 | 1 |
| R2 | 22 | Eab URL 08-04 | 8.4 |
| R7 | 45 | Mab 3299 | 3 |
| R8 | 20 | | |
| R9 | 83 | | |
| R10 | 58 | | |

EXAMPLE 1

Induction of Humoral Immune Responses in Llama

A male llama was immunized with K88ac fimbriae, also known as F4 fimbriae, which were purified from E. coli strain 1087 according to Van Zijderveld et al. (1990). Immunizations were performed both subcutaneously and intramuscularly using 1 ml 50 mg/l K88ac per immunization site. The first two immunizations were performed with a three week interval and using a water in oil emulsion (4:5 (v/v) antigen in water:specol) as described by Bokhout et al. (1981 and 1986). The third and fourth immunization were done without adjuvant, five and nine weeks after the first immunization. The immune response was followed by antigen specific ELISA's.

Method

Polystyrene microtiter ELISA plates (Greiner HC plates) were activated overnight at 4° C. with 100 μl/well of 5 mg/l K88ac antigen in 0.05 M sodium carbonate buffer at pH 9.5. After each incubation plates were washed four times with 0.05% (v/v) TWEEN 20 in demi water in order to remove unbound proteins. The wells were then successively incubated 1 hr at ambient temperature with 100 Fl antibody solution in blocking buffer (PBS containing 2% (w/v) BSA; 0.05% (v/v) TWEEN 20; 1% (v/v) culture supernatant of a S. cerevisiae strain, SU 50 (Giuseppin, et al., 1993) grown on YPD; 1% (v/v) of a cleared lysate of E. coli JM109 cells). The antigen sensitized plates were then successively incubated with (1) serially diluted llama serum samples, (2) 2000-fold diluted polyclonal rabbit anti llama serum (obtained via immunizing rabbits with llama immunoglobulines which were purified via ProtA and ProtG columns), (3) 2000-fold diluted swine-anti-rabbit immunoglobulins conjugated with horse radish peroxidase. The bound peroxidase activity was determined using the substrate 3,3',5,5'-tetramethylbenzidine.

EXAMPLE 2

Cloning, Expressing and Screening of Llama $V_{HH}$ Fragments 2.1 Isolation of Gene Fragments Encoding Llama $V_{HH}$ Domains From an immunized llama a blood sample of about 200 ml was taken and an enriched lymphocyte population was obtained via Ficoll (Pharmacia) discontinuous gradient centrifugation. From these cells, total RNA was isolated by acid guanidium thiocyanate extraction (e.g. via the method described by Chomczynnski and Sacchi (1987). After first strand cDNA synthesis (e.g. with the Amersham first strand cDNA kit), DNA fragments encoding $V_{HH}$ fragments and part of the long or short hinge region where amplified by PCR using specific primers:

```
                                          (see SEQ. ID. NO: 1)
                    PstI
V_H-2B    5'-AGGTSMARCTGCAGSAGTCWGG-3'
```

S=C and G, M=A and C, R=A and G, W=A and T, plasmids contain the GAL7 promoter and PGK terminator sequences as well as the invertase (SUC2) signal sequence. In both plasmids the DNA sequence encoding the SUC2 signal sequence is followed by the first 5 codons (encoding Q-V-Q-L-Q; see SEQ. ID. NO: 4) of the $V_{HH}$ domain (including the BstII site), a stuffer sequence, the last six codons (encoding Q-V-T-V-S-S; see SEQ. ID. NO: 5) of the $V_{HH}$ domain. In pUR4547, this is followed by two stop codons, an AflII and HindIII site. In pUR4548, the Q-V-T-V-S-S sequence is followed by eleven codons encoding the myc-tag, two stop codons, an AflII and HindIII site.

Plasmids pUR4547 and pUR4548 were deposited under the Budapest Treaty at the Centraal Bureau voor Schimmelcultures, Baarn (The Netherlands) on Aug. 18, 1997 with deposition numbers CBS 100012 and CBS 100013, respectively. In accordance with Rule 28(4) EPC, or a similar arrangement from a state not being a contracting state of the EPC, it is hereby requested that a sample of such deposit, when requested, will be submitted to an expert only.

Upon digesting pUR4548 with PstI and BstEII, the about 6.4 kb vector fragment was isolated and ligated with the PstI-BstEII fragments of between 300 and 450 bp obtained as described above. After transformation of S. cerevisiae via electroporation, transformants were selected from minimal medium agar plates (comprising 0.7% yeast nitrogen base, 2% glucose and 2% agar, supplemented with the essential amino acids and bases).

2.3 Screening for Antigen Specific $V_{HH}$ Domains

For the production of llama $V_{HH}$ fragments with myc-tail, individual transformants were grown overnight in selective minimal medium (comprising 0.7% yeast nitrogen base, 2% glucose, supplemented with the essential amino acids and bases) and subsequently diluted ten times in YPGal medium (comprising 1% yeast extract, 2% bacto pepton and 5% galactose). After 24 and 48 hours of growth, the culture supernatant of the colonies was analysed by ELISA for the presence of $V_{HH}$ fragments which specifically bind to the E. coli K88 antigen, in essential the same way as described in Example 1. In this case, however, the presence of specifically bound $V_{HH}$ fragments was detected by incubation with monoclonal anti-myc antibodies, followed by incubation with polyclonal rabbit-anti-mouse conjugate with alkaline phosphatase.

In this way a number of $V_{HH}$ fragments have been obtained, which specifically recognise the E. coli K88 antigen.

```
              HindIII
Lam-07 5'-AACAGTTAAGCTTCCGCTTGCGGCCGCGGAGCTGGGGTCTTCGCTGTGGTGCG-3'    (see SEQ. ID. NO: 2)
(short hinge)

HindIII
Lam-08 5'-AACAGTTAAGCTTCCGCTTGCGGCCGCTGGTTGTGGTTTTGGTGTCTTGGGTT-3'    (see SEQ. ID. NO: 3)
(long hinge)
```

Upon digestion of the PCR fragments with PstI (coinciding with codon 4 and 5 of the $V_{HH}$ domain, encoding the amino acids L-Q) and BstEII (located at the 3'-end of the $V_{HH}$ gene fragments, outside and upstream of the 08 primer coinciding with the amino acid sequence Q-V-T), the DNA fragments with a length between 300 and 450 bp (encoding the $V_{HH}$ domain, but lacking the first three and the last three codons) were purified via gel electrophoresis and isolation from the agarose gel.

2.2 Construction of Saccharomyces cerevisiae Expression Plasmids Encoding Llama $V_{HH}$ Domains Plasmids pUR4547 (CBS 100012) and pUR4548 (CBS 100013) are Saccharomyces cerevisiae episomal expression plasmids, derived from pSY1 (Harmsen et al., 1993). Both Two examples of such fragments are given below:

(see SEQ. ID. NO: 6)

K607
QVQLQESGGG LVQPGGSLRL SCAASGSIFS ASAMTWYRQA

PGKSREYVAR IFFSGGTNYA DSVKGRFTIS RDNAKNTMYL

QMNDLKREDT AVYYCNLLSY WGQGTQVTVS S (see SEQ. ID. NO: 7)

K609
QVQLQESGGG LVQPGGSLRL SCAASGGTFS WYAMGWFRQA

-continued

PGKEREFVAT VSRGGGSTYY ADSVKGRFTI SRDNAKNTVY

LQMNSLKPED TAAYYCAAGR GSPSDTGRPD EYDYWGQGTQ

VTVSS

EXAMPLE 3

Construction of "Self-cloning" Yeast Expression Cassette, Encoding a Chimeric Protein Anchored to the Cell Wall of Yeast, Comprising a Binding Domain and a Cell Wall Anchor In order to display a binding domain at the yeast cell wall, a genetic fusion of the gene encoding the binding domain and a gene encoding the cell wall anchor has to be constructed, either with or with out a linker sequence, essentially as described in WO 94/25591. As an example, the construction of a "self cloned" yeast, displaying a llama $V_{HH}$ fragment fused via the "long hinge" region to the a-agglutinin cell wall anchor will be described below. Obviously this can be done in much the same way for different binding domains, different linkers/hinges and different cell wall anchors.

3.1 Isolation of the Llama "Heavy Chain" Long Hinge Sequence

For the isolation of the hinge regions of the llama "heavy chain" antibodies, the cDNA which was obtained as described in Example 1, was amplified by PCR using the primers $V_H$-2B and Lam-03. The nucleotide sequence of the latter primer was based on a consensus sequence based on the $C_H2$ domains of different species. The PCR reaction resulted in three DNA fragments of about 450 (a), 550 (b) and 850 (c) bp.

```
                                       (see SEQ. ID. NO: 8)
            BamHI
Lam-03    GGTATGGATCCACRTCCACCACCACRCAYGTGACCT
```

Upon digesting these fragments with PstI and BamHI and size fractionation, they were ligated into pEMBL (Dente, 1983) and subjected to nucleotide sequence analysis. The clones obtained from the DNA fragment with an avarage length of ~450 bp (a) were found to comprise a short hinge region, having the following sequence:

For the construction of pUR4588, a NheI site was introduced in the 3'-end of the long hinge region via PCR using the primers:

```
                                       (see SEQ. ID. NO: 11)
                 NheI
BOLI 18   CGCGGCTAGCCTTGGATTCTGTTGTAGGATTGGGTTG (see SEQ. ID. NO: 12)
               BstEII
LH         CCCAGGTCACCGTCTCCTCAGAACCCAAG
``` via which the following sequence:

```
                                       (see SEQ. ID. NO: 13)
   CCTACAACAGAATCCAAGTGTCCCAAGTGTCCA
    P  T  T  E  S  K  C  P  K  C  P
``` became

```
              NheI
CCTACAACAGAATCCAAGGCTAGC               (see SEQ. ID. NO: 14)
 P  T  T  E  S  K  A  S
```

Upon digestion with BstEII and NheI, an about 90 bp fragment was obtained encoding the last 4 amino acids of the $V_{HH}$ domain and the long hinge region except for the last 5 amino acids.

3.2 Adaptation of the α-agglutinin Gene

Plasmid pUR4482 is a yeast episomal expression plasmid for expression of a fusion protein with the invertase signal sequence, the $CH_V09$ variable region, the Myc-tail and the Camel "X-P-X-P" Hinge region (see Hamers-Casterman et al., 1993), and the α-agglutinin cell wall anchor region. For its construction, see WO 94/25591; Example 9 and FIG. 18.

The PstI-site at position 1665 in the α-agglutinin gene was removed via a three step PCR using primers PAF01 to PAF04. For easy cloning and sequencing in pEMBL8, EcoRI and HindIII sites were introduced at the 3'- and 5'-end of the gene fragment encoding α-agglutinin, respectively. PCR-A using primers PAF01 and PAF02 on a pUR4482 template resulted in an about 707 bp fragment with the EcoRI restriction site at the 3'-end. PCR-B using primers PAF03 and PAF04 on a pUR4482 template resulted in an about 427 bp fragment with the HindIII site at the 5'-end. A third PCR was performed with the fragments obtained from reaction A and B, together with the primers PAF01 and PAF04. After digesting the obtained PCR product (~1135 bp), which

```
         V_HH   ><                      short hinge                   >
GGTCACCGTCTCCTCAGCGCACCACAGCGAAGACCCCAGCTCCAAGTGTCCCAAATGCCCA  (see SEQ. ID. NO: 9)
  V  T  V  S  S  A  H  H  S  E  D  P  S  S  K  C  P  K  C  P
                 <-        LAM 07 WB         <-1
```

The clones obtained from the DNA fragment with an average length of ~550 bp (b) was found to comprise a long hinge region, having the following sequence:

comprises the modified α-agglutinin gene without the PstI restriction site, with EcoRI and HindIII, the resulting ~1130 bp fragment was ligated into the vector fragment of

```
BstEII   V_HH   ><                                          long hinge
GGTCACCGTCTCCTCAGAACCCAAGACACCAAAACCACAACCACAACCACAACCACAACCACAACCCAAT  (see SEQ. ID. NO: 10)
  V  T  V  S  S  E  P  K  T  P  K  P  Q  P  Q  P  Q  P  Q  P  N
                 <-        LAM 08 WB         <-1

>
CCTACAAYAGAATCCAAGTGTCCCAAGTGTCCA
 P  T  T  E  S  K  C  P  K  C  P
``` pEMBL8 which was digested with the same enzymes resulting in pRL03.

```
PCR-A
PAF01   GGAATTCGTCTCCTCAGAACAAAAAC      (see SEQ. ID.
                                         NO: 15)
PAF02   GCTGCTGCAAAAGGAATTTA            (see SEQ. ID.
                                         NO: 16)

PCR-B
PAF03   AAATTCCTTTTGCAGCAGC             (see SEQ. ID.
                                         NO: 17)
PAF04   GGGAAGCTTCGACAAAAGCAGAAAAATGA   (see SEQ. ID.
                                         NO: 18)
```

In essentially the same way as for the removal of the PstI site, the SapI site in the α-agglutinin coding sequence at position 1618 was removed from plasmid pRL03. PAF01 and BOLI-20 were used in a PCR reaction with pRL03 as template to generate an approximately 660 bp fragment and primers BOLI19 and PAF04 were used to make an approximately 504 bp fragment which were linked by splicing by overlap extension using primers PAF01 and PAF04 (PCR-C).

```
PCR-A
PAF01     see above
BOLI-20   TTACAAAAGTGGGTTCTTCAGATGGAA   (see SEQ. ID.
                                         NO: 19)

PCR-B
BOLI-19   TTCCATCTGAAGAACCCACTTTTGTAA   (see SEQ. ID.
PAF04     see above                      NO: 20)

PCR-C
Product of PCR-A and PCR-B and PAF01 and PAF04.
```

Again an about 1130 bp EcoRI-HindIII fragment was obtained and cloned in pEMBL8.

Finally, the SacI site at position 2041 can be removed and a HindIII site can be introduced downstream of the stop codon by replacing the sequence:

```
    SacI                                HindIII
    gagctCGGTTCGATCATTTTTCTGCTTTTGTCGAagctt cTCGAGCCAAGCTAGTAAAAAGACGAAAACAGCTTCGAa
    E   L  G  S  I  I  F  L  L  L  S
``` with a synthetic linker having the sequence:

```
(SacI)                                                              HindIII
gagctGGGTTCGATCATTTTTCTGCTTTTGTCGTACCTGCTATTCTAAGATCTGATTAAACGCGTGAagctt  (see SEQ. ID. NO: 21)

cTCGACCCAAGCTAGTAAAAGACGAAAACAGCATGGACGATAAGATTCTAGACTAATTTGCGCACTTCGAa
E   L  G  S  I  I  F  L  L  L  S  Y  L  L  F  *
```

In this way a plasmid was obtained containing an about 990 bp NheI-HindIII fragment encoding the C-terminal 320 amino acids of the α-agglutinin in which the PstI, SapI and SacI sites were removed via silent mutations in order to facilitate further construction work.

3.3 Construction of pUR4588

The following fragments were subsequently joined:
i) the about 100 bp SacI-PstI fragment of pUR4548: comprising a part of the Gal7 promoter, the SUC2 nucleotide sequence and the first 4 codons of the $V_{HH}$ fragment,
ii) the about 350 bp PstI-BstEII fragment, which was obtained as described in Example 2: encoding a truncated $V_{HH}$ fragment, missing both the first 4 (QVQL; see SEQ. ID. NO: 4) and the last 5 (VTVSS; see SEQ. ID. NO: 5) amino acids of the $V_{HH}$ fragment,
iii) the about 90 bp BstEII-NheI fragment obtained as described in Example 3.1: encoding the last 5 amino acids of the $V_{HH}$ fragment and the long hinge region, and
iv) the about 1 kb NheI-HindIII fragment obtained as described in 3.2: the adapted α-agglutinin gene.

Figure 5:
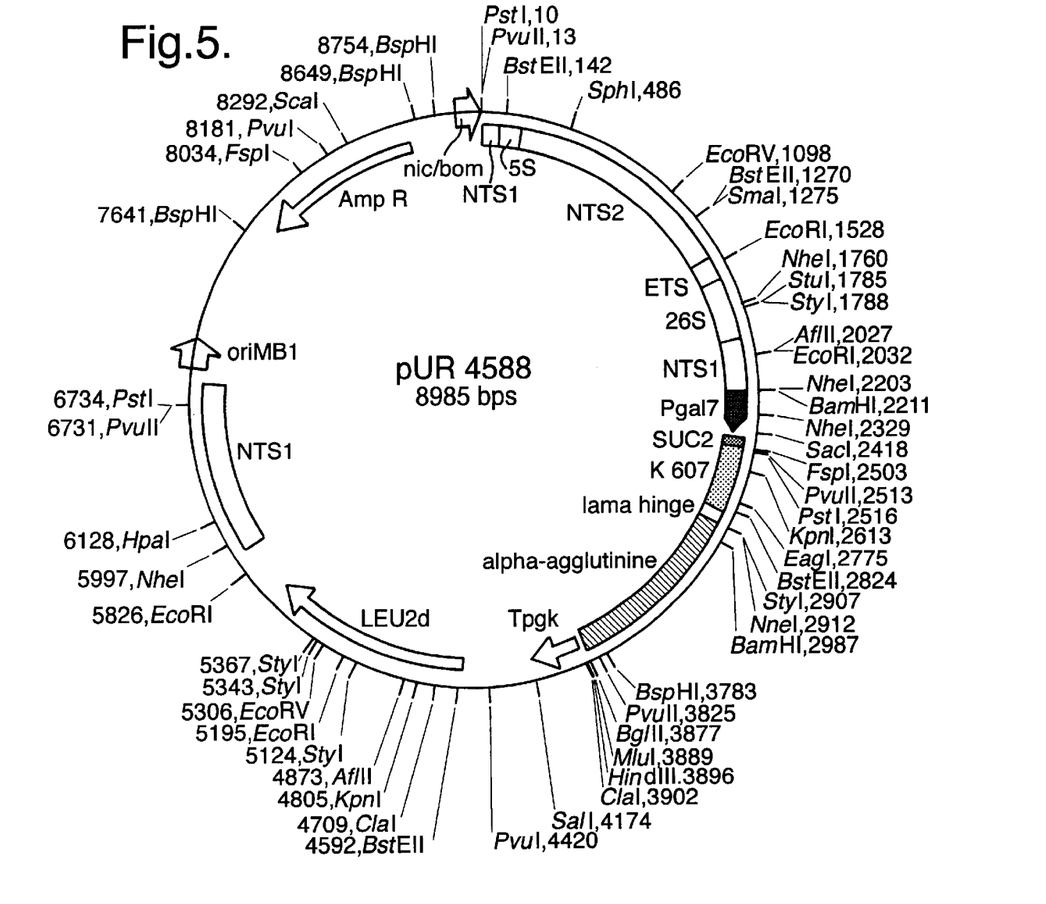
FIG. 5 represents a restriction map of plasmid pUR 4588.

Finally, the thus obtained about 1.5 kb SacI-HindIII fragment was ligated into the about 7.5 kb vector fragment of pUR2822 which was digested with the same enzymes, resulting in pUR4588 (FIG. 7).

Plasmid pUR2822 was deposited under the Budapest Treaty at the Centraal Bureau voor Schimmelcultures, Baarn (The Netherlands) on Sep. 29, 1998 with deposition number CBS 101292. In accordance with Rule 28(4) EPC, or a similar arrangement from a state not being a contracting state of the EPC, it is hereby requested that a sample of such deposit, when requested, will be submitted to an expert only.

3.4 Production of Yeast Strains "Functionally" Expressing the Chimeric Protein

Plasmid pUR4588 was digested with SapI, after which an about 6.7 kb fragment was purified, via gel electrophoresis and isolated from the agarose gel. This fragment was introduced into yeast strains via electroporation. Transformants containing (multicopies of) the DNA fragment integrated into the rDNA locus of their genome were selected as described in Example 2. Induction of the production and display of the binding domain was also done as described in Example 2. In order to determine the functionality of the binding domains displayed at the yeast cell wall, the following assay was performed:

GI-ELISA

The yeast cells were diluted in PBS containing 0.05% (v/v) TWEEN 20 (PBST) to an $A_{660}$=1 and 10 μl of this suspension was mixed with 1 μg K88ac antigen in 100 μl PBST in an Eppendorf tube and incubated for 1 hr at ambient temperature. Unbound antigen was removed from the yeast cells by three washes in 1 ml PBST. Cells were collected after each wash by centrifugation and aspiration of the supernatant. The yeast cells were subsequently resuspended in 100 μl of PBST containing a conjugate of monoclonal antibody AD11, which is specific for K88, and horse radish peroxidase (AD11-HRPO; Van Zijderveld et al., 1990). After 1 hr incubation at ambient temperature the cells were washed again three times with PBST. The amount of AD11-HRPO bound to the yeast cells was taken as a measure of the amount of functional K88-binding domains displayed at the yeast cell wall. This value was determined by performing a peroxidase assay on serial twofold dilutions of these cells, using 3,3',5,5'-tetramethylbenzidine as a substrate, and measuring the $A_{450}$. The recovered functionality (RF) of the displayed antibody fragments after a physical treatment to inactivate the S. cerevisae cells is defined as the A450 before treatment (is F0) divided by the $A_{450}$ after treatment (is Ft).

EXAMPLE 4

Heat Inactivation of $V_{HH}$s

4.1 Production of Biomass Suspension

Saccharomyces cerevisiae strain SU50 containing the genomically integrated expression plasmid pUR4588 was used. The strain was grown in a 10 l scale fermentor using a fed batch fermentation set up (Mendoza-Vega et al., 1994). Such a fermentation consists of two steps: the first step (the batch phase) is performed in a Yeast extract and Peptone (YP) medium containing glucose. In the second step (the feed phase) YP medium is added containing glucose and galactose, in order to induce the promoter for the production of the $V_{HH}$-agglutinine fusion. In this way a culture was obtained with a cell density of about $10^9$–$10^{10}$ per ml, comparable to large scale fermentations.

Cell density or viable counts (N) were determined by making decimal dilutions of a cell culture in sterile pepton physiological salt (PFS; 0.85% NaCl, 0.1% Bactopepton (Difco), pH 7). Samples of these dilutions were plated on YPD agar and incubated for 5 days at 30° C. after which the number of colonies were counted. The reduction of viable counts (RVC) after treatment to inactivate the S. cerevisiae cells is defined as the logarithm of the viable counts after treatment (is Nt) divided by the number of viable counts before treatment (is N0); Log (Nt/N0).

4.2 Heat Treatment

Determination of the killing efficiency of heat treatment on high cell density cultures was performed using one of two different approaches, as desired.

4.2.1 Using Glass Capillaries

Sterile glass capillaries (Fisher Scientific Den Bosch, l=100 mm, d=2 mm) were filled with 0.1 ml of the yeast culture medium and sealed. After incubating the filled, sealed capillaries, they were placed for a set time in a water bath at the desired temperature (experiments were performed at quadruplets). After this the recovered functionality (RF) and the reduction in viable counts (RVC) for the different samples was determined as described above.

4.2.2 Using Aluminium Vials

Sterile aluminium cryo vials (Omnilabo, volume 3 ml) were filled with 0.5 ml of the yeast culture for each temperature/time combination (experiments performed in duplo). The vials were placed in a water bath at the desired temperature and time. After this the recovered functionality (RF) and the reduction in viable counts (RVC) for the different samples was determined as described above.

4.3 Viable Counts and GI-ELISA

From the yeast culture the viable counts (N0) and the GI-ELISA signal (F0) was determined before heat treatment. The same was done for the samples obtained as described above (Nt and Ft, respectively). The results are presented in Table 3 below.

TABLE 3

| Temp (° C.) | time (sec) | RVC (= log (Nt/NO)) | RF (= Ft/FO) |
| --- | --- | --- | --- |
| 60 | 300 | −4 | 100% |
| 62 | 60 | >−6 | 100% |
| 70 | 30 | >−7 | >85% |
| 74 | 15 | >−7 | >85% |

EXAMPLE 5

Inactivation of S. cerevisiae SU50 (pUR 4588) with Ultra High Pressure

From literature it is known that at pressures over 300 MPa proteins FF ATP-ase can be inactivated (Wouters et al, 1998).

S. cerevisiae SU50 (pUR4588), displaying anti-E. coli K88 $V_{HH}$ fragments, was grown at 10 liter scale as described above. Samples of 1.5 ml were taken and transferred to bags for Ultra High Pressure treatment in a "Food Lab Multi Vessel" (Stansted Fluid Power, UK). Samples were incubated at three different pressures 250, 300 and 325 Mpa for different periods of time. The survival of the yeast cells and the functionality of the displayed $V_{HH}$s was determined as described above. The results are presented in Table 4 below.

TABLE 4

| Pressure (Mpa) | time (min) | RVC (= log (Nt/NO)) | RF (= Ft/FO) |
| --- | --- | --- | --- |
| 250 | 60 | −9 | 100% |
| 300 | 3 | −6 | >70% |
|  | 20 | −9 | >70% |
| 325 | 1 | −6 | 70% |
|  | 3 | −9 | 70% |
|  | 20 | −9 | 70% |

It was further found that yeast cells that do not have the capacity to synthesize trehalose are much more sensitive for UHP (Fernandes et al., 1997). Therefore, a preferred embodiment of the inactivation of yeast with UHP is, instead of using a wild type yeast strain, using a variant strain defective in the synthesis of trehalose, e.g. a strain in which the TPS1 gene has been inactivated e.g. by partial or complete deletion. In this way the UHP treatment could be reduced from 300 MPa to 200 MPa with the same reduction in viable counts.

EXAMPLE 6

Killing of Yeast Cells by Irradiation

An alternative for the inactivation of yeast cells is gamma radiation. S. cerevisiae SU50 (pUR4588), was grown at 10 liter scale as described above. After fermentation the biomass slurry was transferred to polypropylene drums and exposed to 10 kGray or 25 kGray of gamma radiation ('Gammaster', Ede). The survival of the yeast cells and the functionality of the displayed $V_{HH}$s was determined as described above. For both cases, the RVC was better than −10 (no viable counts left after irradiation), whereas the RF of the $V_{HH}$s was 100%. The anti-K88 activity was not affected by the irradiation.

A number of genes involved in DNA repair are known (e.g rad9, rad30, rad52, sir2, sir3, sir4). Yeast strains carrying mutations in these genes, are known to be more sensitive towards radiation (Friedberg et al., 1991; Tsukamoto et al., 1997). In a preferred embodiment of this invention, a yeast strain with one or more mutations in one or more of these genes is used.

EXAMPLE 7

Combined Effect of Heat Inactivation and Antimicrobials on Saccharomyces cerevisiae S. cerevisiae SU50 (pUR4588) cells were cultivated and harvested as described above and subjected to heat treatment as described above in the presence of antimicrobials like ethanol, potassium sorbate and antimicrobial peptides like nisin and MB21. According to the methods described in the previous examples the inactivation efficiency and the recovery of the functionality of the $V_{HH}$ antibodies have been determined. The results are given in Table 5 below.

TABLE 5

Inactivation of *S. cerevisiae* and $V_{HH}$ as function of the temperature and the concentration of antimicrobials

| Temp (° C.) | Antimicrobials | Time (min) | RVC (= log Nt/No) | RF (= Ft/Fo) |
|---|---|---|---|---|
| 50 | 3% ethanol | 60 | 0 | 100% |
| 50 | 0.2% K-sorbate | 60 | 0 | 100% |
| 60 | — | 5 | −4 | 100% |
| 60 | 3% ethanol | 5 | −7 | 90% |
| 60 | 0.2% K-sorbate | 5 | −8 | 95% |

It has been reported that yeast cells that do not have the full capacity of synthesising multi drug resistant proteins are much more sensitive to weak acids, e.g. sorbic acid (PDR12; Piper et al., 1998). Therefore, a preferred embodiment of inactivation of yeast by a combination of heat and acid is to use, instead of the wild type yeast strain, a strain in which the PMR gene is inactivated, e.g. via partial or complete deletion. In this way either the temperature or the amount of acid or both can be reduced considerably.

EXAMPLE 8

Animal Feeding Trials with Yeast Displaying Anti *E. coli* K88 $V_{HH}$s on Their Surface In this experiment two groups of piglets were used. A mild *E. coli* K88 infection was induced in all animals by an oral dose of $10^6$ *E. coli* K88 cells. For group I (exp. group) the feed was supplemented with 6 ml of a concentrated suspension ($10^{10}$–$10^{11}$ cells per ml) of SU50 (pUR4588), and for group II (control) with the same amount of wild type SU50 yeast. The yeast cells were inactivated with gamma irradiation according to the procedure as described in Example 6.

Number of affected piglets due to dosing of >$10^6$ *E. coli* K88/g in the meal. See Table 6 below.

TABLE 6

| Day | Control | Exp group |
|---|---|---|
| 0 | 0 | 0 |
| 1 | 22 | 17 |
| 2 | 50 | 19 |

Conclusion: protective effect clearly visible after 2 days.

REFERENCES

Bokhout, B. A., Van Gaalen, C., and Van Der Heijden, Ph. J., (1981), A selected water-in-oil emulsion: composition and usefulness as an immunological adjuvant. Vet. Immunol. Immunopath., 2:491–500.

Bokhout, B. A., Bianchi, A. T. J., Van Der Heijden, Ph. J., Scholten, J. W. and Stok, W., (1986), The influence of a water-in-oil emulsion on humoral immunity. Comp. Immun. Microbiol. Infect. Dis., 9:161–168.

Chomczynnski, P. and Sacchi, N. (1987) Single step method of RNA isolation by acid guanidium thiocyanate-phenol-chloroform extraction. Analytical Biochem. 162:156–159.

Dente, L., Cesareni, G., Cortese, R. (1983) pEMBL—A new family of single stranded plasmids Nucleic Acids Research 11:1645–1655.

Fernandes, P. M. B., Panek, A. D., and Kurtenbach, E. (1997) Effect of hydrostatic pressure on a mutant of *Saccharomyces cerevisiae* deleted in the trehalose-6-phosphate synthase gene. FEMS Microbiolology letters 152:17–21.

Friedberg, E. C., Siede, W. and Cooper, A. J. (1991) Cellular responses to DNA damage in yeast pp 147–192 in: The Molecular and Cellular Biology of the Yeast *Saccharomyces cerevisiae*. Eds. Broach, J. R, Pringel, J. R and Jones, E. W. Cold Spring Harbor Laboratory Press.

Giuseppin, M. L. F., Almkerk, J. W., Heistek, J. C., Verrips, C. T., (1993) Comparative Study on the Production of Guar Alpha-Galactosidase by *Saccharomyces cerevisiae* SU50B and *Hansenula polymorpha* 8/2 in Continuous Cultures. Applied and Environmental Microbiology 59:52–59.

Mendoza-Vega, O., Sabatie, J, & Brown, S. W. (1994) Industrial-production of heterologous proteins by fed-batch cultures of the yeast *Saccharomyces cerevisiae*. FEMS Microbiology Reviews 15:369–410.

Piper, P., Mahe, Y., Thompson, S., Pandjaitan, R., Holyoak, C., Egner, R., Muhlbauer M., Coote P. and Kuchler, K. (1998) The pdr12 ABC transporter is required for the development of weak organic acid resistance in yeast. EMBO J. 17:4257–4265.

Tsukamoto, Y., Kato, J. and Ikeda, H., (1997) Silencing Factors participate in DNA-Repair and Recombination in *Saccharomyces cerevisiae*. Nature 388:900–903.

Van der Vaart, J. M. and C. T. Verrips (1998), Cell wall proteins of *S. cerevisiae*, Biotechnology and Genetic Engineering Reviews 15:387–411.

Wouters, P. C., Glaasker, E., Smelt, J. P. P. M., (1998) Effects of high pressure on inactivation kinetics and events related to proton efflux in *Lactobacillus plantarum* Applied And Environmental Microbiology 64:509–514.

Zijderveld, F. G. et al., (1990) Epitope analysis of the F4 (K88) fimbrial antigen complex of enterotoxigenic *E. coli* using monoclonal antibodies. Infection and Immunity, 58:1870–1878.

What is claimed is:

1. A product comprising inactivated lower eukaryotic cells having expressed and immobilised at their outer surface one or more functionally active heavy chain antibodies from an animal belonging to the family Camelidae or one or more functionally active fragments thereof, wherein said one or more antibodies or functionally active fragments thereof retain their functionality by over 60% after the lower eukaryotic cells are inactivated.

2. The product of claim 1, wherein said at least one antibody fragment is a variable domain.

3. The product of claim 1, which is selected from the group consisting of food products, personal care products, and animal feed products.

4. The product of claim 1, wherein the viability of the lower eukaryotic cells has been reduced by a factor of at least $10^6$ after the inactivation.

5. The product of claim 1, wherein the lower eukaryotic cells are inactivated by physical treatment.

6. The product of claim 1, wherein the lower eukaryotic cells are inactivated by chemical treatment.

7. The product of claim 6, wherein the chemical treatment comprises treating the lower eukaryotic cells with an effective amount of at least one compound selected from the group consisting of an antimicrobial agent and a cell wall degrading enzyme.

8. The product of claim 1, wherein the lower eukaryotic cells are inactivated by a combination of physical and chemical treatment.

9. The product of claim 1, wherein the functionally active antibody fragments specifically recognise one or more pathogenic microorganisms, having a binding constant of larger than $10^6$.

10. The product of claim 1, wherein the functionally active antibody fragments specifically recognise a toxin having a binding constant of larger than $10^6$.

11. The product of claim 1, wherein the functionally active antibody fragments specifically recognise spoilage microorganisms with binding constant of larger than $10^6$.

12. Animal feed products containing inactivated yeast cells having expressed and immobilised on their surface one or more functional heavy chain antibodies specific to microorganisms pathogenic to animals or functionally active fragments thereof from an animal belonging to the family Camelidae, wherein said one or more antibodies or functionally active fragments thereof retain their functionality by over 60% after the lower eukaryotic cells are inactivated.

13. Animal feed products of claim 12, wherein the inactivated yeast cells have anti-*E. coli* K88 llama antibodies or functionally active fragments thereof on their surface.

14. The animal feed products of claim 12, wherein the yeast cells are *Saccharomyces cerevisiae* cells.

15. A product comprising inactivated lower eukaryotic cells, which have expressed therein one or more heavy chain antibodies specific for a pathogenic microorganism or functionally active fragments thereof obtained from an animal belonging to the family Camelidae such that said one or more heavy chain antibodies or functionally active fragments are immobilised at the outer surface of said lower eukaryotic cells, and wherein said lower eukaryotes have been inactivated by killing them with an efficiency of greater than $10^6$; wherein said one or more antibodies or functionally active fragments thereof protect a subject against infection by said pathogenic microorganism, and wherein functionality of said one or more antibodies or functionally active fragments thereof is retained by over 60% after inactivation of said lower eukaryotic cells.

16. The product of claim 15, wherein said lower eukaryotic cells have been inactivated by at least physical treatment.

17. The product of claim 15, wherein said lower eukaryotic cells have been inactivated by at least chemical treatment.

18. The product of claim 15, wherein said pathogenic microorganism is selected from the group consisting of *E. coli*, Salmonella, Shigella, and animal viruses.

19. A method of making the product of claim 15 comprising:
   (a) expressing one or more heavy chain antibodies or functionally active fragments thereof in lower eukaryotic cells, wherein said one or more heavy chain antibodies or functionally active fragments thereof are obtained from an animal belonging to the family Camelidae, are specific for a pathogenic microorganism, and protect a subject against infection by said pathogenic microorganism;
   (b) immobilising said one or more active heavy chain antibodies or functionally active fragments thereof at the outer surface of said lower eukaryotic cells; and
   (c) inactivating said lower eukaryotic cells by killing them with an efficiency of greater than $10^6$, wherein functionality of said one or more antibodies or functionally active fragments thereof is retained by over 60% after said lower eukaryotic cells are inactivated.

20. A method of using the product of claim 15 comprising feeding said product to a subject in need of protection against said infection by said pathogenic microorganism.

21. A product to which has been added lower eukaryotic cells, which have expressed therein one or more heavy chain antibodies specific for a pathogenic microorganism or functionally active fragments thereof obtained from an animal belonging to the family Camelidae such that said one or more heavy chain antibodies or functionally active fragments are immobilised at the outer surface of said lower eukaryotic cells, and said lower eukaryotic cells have been inactivated by killing them with an efficiency of greater than $10^6$; wherein said one or more antibodies or functionally active fragments thereof protect a subject against infection by said pathogenic microorganism, and wherein functionality of said one or more antibodies or functionally active fragments thereof is retained by over 60% after inactivation of said lower eukaryotic cells.

22. The product of claim 20, wherein said product is selected from the group consisting of food products, personal care products, cosmetics and animal feed.

* * * * *

SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: primer_bind

<400> SEQUENCE: 1

```
aggtsmarct gcagsagtcw gg                                              22
```

<210> SEQ ID NO 2
<211> LENGTH: 53
<212> TYPE: DNA
<213> ORGANISM: Artificial Sequence
<220> FEATURE:
<223> OTHER INFORMATION: Description of Artificial Sequence: primer_bind

<400> SEQUENCE: 2

```
aacagttaag cttccgcttg cggccgcgga gctggggtct cgctgtggt gcg            53
```

<210> SEQ ID NO 3
<211> LENGTH: 53
<212> TYPE: DNA
<213> ORGANISM: Artificial Sequence
<220> FEATURE:
<223> OTHER INFORMATION: Description of Artificial Sequence: primer_bind

<400> SEQUENCE: 3

```
aacagttaag cttccgcttg cggccgctgg ttgtggtttt ggtgtcttgg gtt           53
```

<210> SEQ ID NO 4
<211> LENGTH: 5
<212> TYPE: PRT
<213> ORGANISM: llama

<400> SEQUENCE: 4

Gln Val Gln Leu Gln
 1               5

<210> SEQ ID NO 5
<211> LENGTH: 6
<212> TYPE: PRT
<213> ORGANISM: llama

<400> SEQUENCE: 5

Gln Val Thr Val Ser Ser
 1               5

<210> SEQ ID NO 6
<211> LENGTH: 111
<212> TYPE: PRT
<213> ORGANISM: llama

<400> SEQUENCE: 6

Gln Val Gln Leu Gln Glu Ser Gly Gly Leu Val Gln Pro Gly Gly
 1               5                  10                  15

Ser Leu Arg Leu Ser Cys Ala Ala Ser Gly Ser Ile Phe Ser Ala Ser
                20                  25                  30

Ala Met Thr Trp Tyr Arg Gln Ala Pro Gly Lys Ser Arg Glu Tyr Val
            35                  40                  45

Ala Arg Ile Phe Phe Ser Gly Gly Thr Asn Tyr Ala Asp Ser Val Lys
        50                  55                  60

Gly Arg Phe Thr Ile Ser Arg Asp Asn Ala Lys Asn Thr Met Tyr Leu
 65                  70                  75                  80

Gln Met Asn Asp Leu Lys Arg Glu Asp Thr Ala Val Tyr Tyr Cys Asn
                85                  90                  95

Leu Leu Ser Tyr Trp Gly Gln Gly Thr Gln Val Thr Val Ser Ser
            100                 105                 110

```
<210> SEQ ID NO 7
<211> LENGTH: 125
<212> TYPE: PRT
<213> ORGANISM: llama

<400> SEQUENCE: 7

Gln Val Gln Leu Gln Glu Ser Gly Gly Gly Leu Val Gln Pro Gly Gly
  1               5                  10                  15

Ser Leu Arg Leu Ser Cys Ala Ala Ser Gly Gly Thr Phe Ser Trp Tyr
             20                  25                  30

Ala Met Gly Trp Phe Arg Gln Ala Pro Gly Lys Glu Arg Glu Phe Val
         35                  40                  45

Ala Thr Val Ser Arg Gly Gly Gly Ser Thr Tyr Tyr Ala Asp Ser Val
     50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Ala Tyr Tyr Cys
                 85                  90                  95

Ala Ala Gly Arg Gly Ser Pro Ser Asp Thr Gly Arg Pro Asp Glu Tyr
            100                 105                 110

Asp Tyr Trp Gly Gln Gly Thr Gln Val Thr Val Ser Ser
        115                 120                 125

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: primer_bind

<400> SEQUENCE: 8
ggtatggatc cacrtccacc accacrcayg tgacct                        36

<210> SEQ ID NO 9
<211> LENGTH: 61
<212> TYPE: DNA
<213> ORGANISM: Artificial Sequence
<220> FEATURE:
<223> OTHER INFORMATION: Description of Artificial Sequence: CDS

<400> SEQUENCE: 9
ggtcaccgtc tcctcagcgc accacagcga agacccagc tccaagtgtc ccaaatgccc    60
a                                                                   61

<210> SEQ ID NO 10
<211> LENGTH: 112
<212> TYPE: DNA
<213> ORGANISM: Artificial Sequence
<220> FEATURE:
<223> OTHER INFORMATION: Description of Artificial Sequence: CDS

<400> SEQUENCE: 10
ggtcaccgtc tcctcagaac ccaagacacc mcataaaccy acaaccaymc aaccacaacc    60
yacaaccaca acyccaatcc tacaayagaa tccaagtgtc yccaagtgtc ca           112

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: primer_bind
```

```
<400> SEQUENCE: 11
cgcggctagc cttggattct gttgtaggat tgggttg                              37

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer_bind

<400> SEQUENCE: 12
cccaggtcac cgtctcctca gaacccaag                                      29

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: CDS

<400> SEQUENCE: 13
cctacaacag aatccaagtg tcyccaagtg tcca                                34

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: CDS

<400> SEQUENCE: 14
cctacaayca gaatccaagg ctagc                                          25

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: primer_bind

<400> SEQUENCE: 15
ggaattcgtc tcctcagaac aaaaac                                         26

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: primer_bind

<400> SEQUENCE: 16
gctgctgcaa aaggaattta                                                20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: primer_bind

<400> SEQUENCE: 17
aaattccttt tgcagcagc                                                 19

<210> SEQ ID NO 18
<211> LENGTH: 29
```

```
<212> TYPE: DNA
<213> ORGANISM: Artificial Sequence
<220> FEATURE:
<223> OTHER INFORMATION: Description of Artificial Sequence: primer_bind

<400> SEQUENCE: 18
gggaagcttc gacaaaagca gaaaaatga                                      29

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: primer_bind

<400> SEQUENCE: 19
ttacaaaagt gggttcttca gatggaa                                        27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: primer_bind

<400> SEQUENCE: 20
ttccatctga agaacccact tttgtaa                                        27

<210> SEQ ID NO 21
<211> LENGTH: 72
<212> TYPE: DNA
<213> ORGANISM: Artificial Sequence
<220> FEATURE:
<223> OTHER INFORMATION: Description of Artificial Sequence: CDS (part)
     + non-translat. (part)

<400> SEQUENCE: 21
gagctgggtt cgatcatttt tctgcttttg tcgtacctgc tattctaaga tctgattaaa    60
cgcgtgaagc tt                                                        72
```